United States Patent
Bobo, Sr. et al.

(10) Patent No.: US 8,360,988 B2
(45) Date of Patent: Jan. 29, 2013

(54) CATHETER AIR MANAGEMENT SYSTEM

(75) Inventors: Donald E. Bobo, Sr., Fountain Valley, CA (US); David Robbins Asbury, Lake Elsinore, CA (US)

(73) Assignee: InnerSpace, Inc., Tustin, CA (US)

( * ) Notice: Subject to any disclaimer, the term of this patent is extended or adjusted under 35 U.S.C. 154(b) by 59 days.

(21) Appl. No.: 12/606,169

(22) Filed: Oct. 26, 2009

(65) Prior Publication Data

US 2010/0113968 A1    May 6, 2010

Related U.S. Application Data

(60) Provisional application No. 61/197,042, filed on Oct. 24, 2008, provisional application No. 61/209,839, filed on Mar. 12, 2009.

(51) Int. Cl.
*A61B 5/00* (2006.01)
(52) U.S. Cl. ...................................................... 600/561
(58) Field of Classification Search .................. 600/561; 604/97.01, 97.02, 131, 132, 143, 146
See application file for complete search history.

(56) References Cited

U.S. PATENT DOCUMENTS

| | | | |
|---|---|---|---|
| 2,866,453 A * | 12/1958 | Jewett | 600/487 |
| 3,662,743 A | 5/1972 | Amarante et al. | |
| 3,714,869 A * | 2/1973 | Flory et al. | 91/434 |
| 3,719,070 A * | 3/1973 | Hanes | 73/37 |
| 3,884,242 A | 5/1975 | Bazell et al. | |
| 4,077,394 A | 3/1978 | McCurdy | |
| 4,301,811 A | 11/1981 | Layton | |
| 4,776,347 A | 10/1988 | Matthews | |
| 4,901,735 A | 2/1990 | Von Berg | |
| 4,903,707 A | 2/1990 | Knute et al. | |
| 4,934,375 A | 6/1990 | Cole et al. | |
| 5,573,007 A | 11/1996 | Bobo, Sr. | |
| 5,644,285 A | 7/1997 | Maurer | |
| 5,984,879 A | 11/1999 | Wallace et al. | |
| 6,231,524 B1 | 5/2001 | Wallace et al. | |
| 6,447,462 B1 | 9/2002 | Wallace et al. | |
| 7,654,967 B2 | 2/2010 | Bobo, Sr. | |
| 2002/0151854 A1 * | 10/2002 | Duchon et al. | 604/197 |

FOREIGN PATENT DOCUMENTS

| | | |
|---|---|---|
| EP | 0 846 472 A1 | 6/1998 |
| EP | 0 972 535 A2 | 1/2000 |
| GB | 968376 A | 9/1964 |
| GB | 2 318 513 A | 10/1997 |

* cited by examiner

*Primary Examiner* — Max Hindenburg
(74) *Attorney, Agent, or Firm* — Inskeep IP Group, Inc.

(57) ABSTRACT

An air management system is described for removing and reintroducing a desired amount of air into an air passage of a pressure measurement catheter. More specifically, the system includes a cylindrical housing, check valves in communication with the housing and an moveable shaft with multiple sealing members along its length. As the shaft is moved within the housing, a piston member causes the residual air in the catheter air passage to be evacuated to a defined negative pressure. Further movement of the shaft causes a piston member to inject a predetermined volume of air into the catheter air passage. In this respect, periodic adjustments of the piston member returns the volume of air in a variable volume chamber to one that is unaffected by residual volume in the chamber and that provides an optimum volume of air to maximize the time the sensor can function accurately between recharging events.

20 Claims, 5 Drawing Sheets

US 8,360,988 B2

CATHETER AIR MANAGEMENT SYSTEM

RELATED APPLICATIONS

This application claims priority to U.S. Provisional Application Ser. No. 61/197,042 filed Oct. 24, 2008 entitled Catheter Air Management System, and U.S. Provisional Application Ser. No. 61/209,839 filed Mar. 12, 2009 entitled Catheter Air Management System, all of which are hereby incorporated herein by reference.

BACKGROUND OF THE INVENTION

Presently, biologically compatible air-based pressure monitoring catheters are used in a number of medical applications to monitor pressure at various locations within a mammalian body. For example, air-based pressure monitoring catheters may be inserted into the skull of a patient thereby permitting the external monitoring of intra-cranial pressure.

Currently, a number of air-based pressure monitoring catheters have been developed. Generally, these air-based pressure monitoring catheters comprise a catheter having an air lumen formed therein which communicates with a bladder positioned at or near its distal end. In addition, the catheter includes a connector located at or near its proximal end which may be connected to an external pressure transducer. During use, the volume of the bladder attached to the catheter changes as pressure varies in accordance with Boyle's Law ($P_1 V_1 = P_2 V_2$). As a result, the pressure of the gas within the catheter becomes equal to that of the environment surrounding the bladder. The media surrounding the bladder must be capable of movement to accommodate the variations in bladder volume as pressure changes.

The use of air-based pressure monitoring catheters in low or negatively pressurized environments has proven problematic. When the proximal connector is open to atmospheric pressure in the process of periodically replacing air lost by diffusion through the bladder, the external pressure extant in the body site monitored on a bladder will expel residual air from the bladder. If the pressure is low or negative, a significant amount of residual air may remain in the bladder. The amount of air injected is intended to be sufficient to keep the bladder in an active state for a period of 8 hours. If this volume is added to the residual air in a bladder that has not been completely collapsed by the environment around it, the sum of the residual air and injected air exceed the intrinsic volume of a fully shaped bladder. Should this happen, a positive pressure is established in the bladder. The bladder is now unable to read pressure below the internal pressure created.

Air management systems such as those seen in U.S. Pub. No. 2007/0208270 and U.S. Pat. No. 6,447,462, which are both herein incorporated by reference, allow a user to adjust the amount of air in a system. For example, these systems allow a user to vent the air passage of the catheter to the open environment, then charge the passage with an amount of air. While these systems function adequately when residual air in the bladder is adequately expressed by pressure from the monitored body site, they over pressurize the bladder if the monitored site pressure has not sufficiently collapsed the bladder prior to the injection of air. An optional design that avoids over pressurizing the bladder by reducing the amount of air injected is not attractive as the lessor amount of air injected reduces the effective operating time between air recharging events in a case where the bladder has been largely collapsed by pressure in the body site measured. The intent of the invention is to preserve the desired operating time between air-charging events in a manner that precludes the possibility of pressurizing the bladder.

SUMMARY OF THE INVENTION

A preferred embodiment according to the present invention includes an air management system for removing and reintroducing a desired amount of air into an air passage of a pressure measurement catheter. More specifically, the system includes three cylinders within which can move a shaft with three sealing members along its length. The system includes check valves in communication with one of the cylinders. As the shaft is moved within the set of cylinders, it causes the residual air in the catheter air passage to be evacuated to a negative pressure defined by one check valve. Further movement of the piston member injects a predetermined volume of air into the catheter air passage. This air is from excess air present in the evacuation cylinder and held by a check valve at a predetermined pressure (e.g., 0.5 PSI), not from exposure to the open atmosphere. Evacuating the catheter to a fixed negative pressure prior to injecting air eliminates the possibility that variations in the residual volume in the bladder can affect the pressure reading or the operating time.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
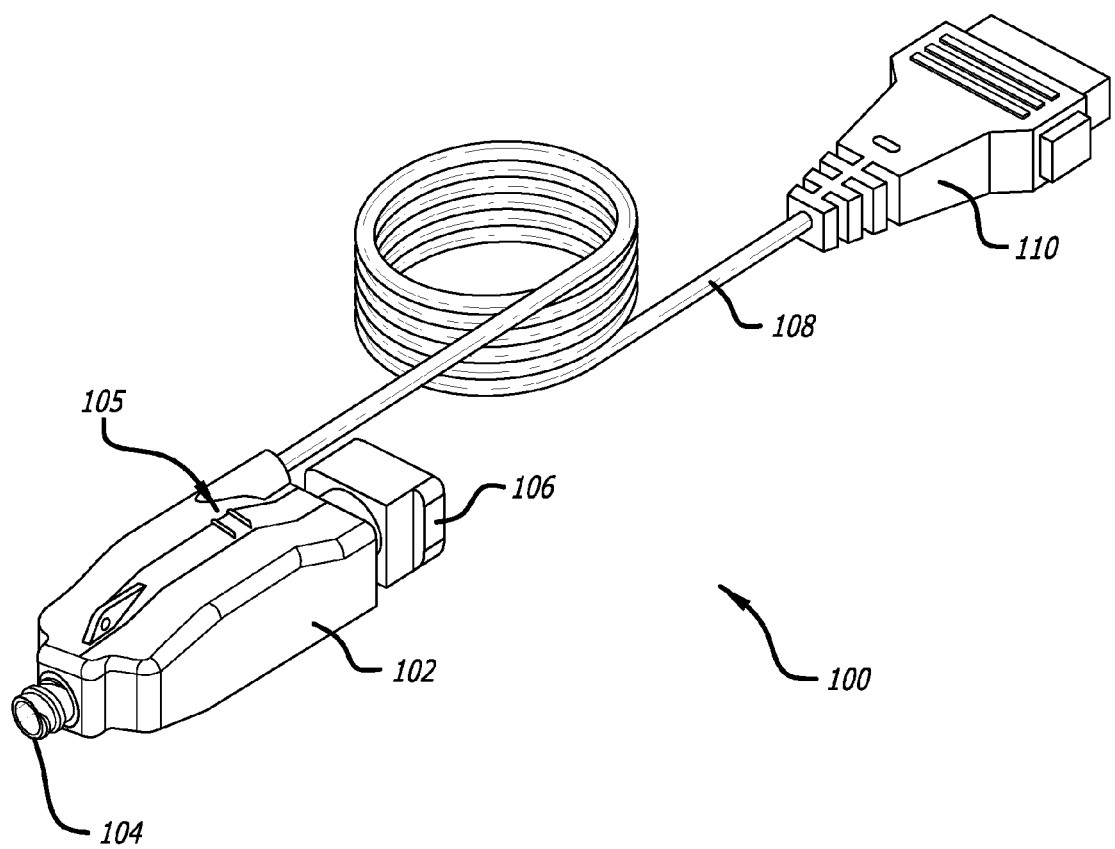
FIG. 1 illustrates a perspective view of a catheter air management system according to a preferred embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 illustrates an air catheter management system 100 according to a preferred embodiment of the present invention. The system 100 allows a user to charge an air passage in communication with a catheter having a pressure sensing lumen (e.g., such as that shown in U.S. Provisional Applications 61/197,039 and 61/197,041, the contents of which are hereby incorporated by reference). The air passage of the catheter is connected to the catheter connection port 104.

The system 100 also includes a monitor cable 108 that communicates between a pressure monitor (not shown) and a transducer 115 (FIG. 2) within the housing 102. The monitor cable preferably includes multiple wires that provide an excitation voltage for the transducer and voltage measurements to the monitor. A monitor connector 110 (e.g., a Marquette connector) connects to a desired monitor type to display a pressure reading to a user.

Proper operation of an air-based pressure sensor requires that a predetermined amount of air reside in the bladder. Over time, air can diffuse out of the catheter, the pressure lumen of the catheter, or other portions of the arrangement. The system 100 allows the user to periodically replace air lost by diffusion by pulling out a handle 106, then pushing that handle back into to the housing 102 of the system 100. This action removes the air in the system 100 to a predetermined vacuum pressure, and then adds a predetermined amount of air back into the system.

Preferably, the housing further includes a set of indicators 105, such as lights, that indicate when the expected operating life of the sensor between recharging events has been reached and a recharging event is required. Preferably, the housing 102 (or optionally the transducer) may include a timer that counts a predetermined period of time (e.g., 8 hours) before signaling that it is time to recharge (i.e., pull out the handle 106 and push in the handle 106).

Further, the housing 102 may include a microprocessor or other electronics that connects to the transducer 115 to obtain a pressure reading, then convert this reading to a form recognizable to the pressure monitor (e.g., mV/mmHg/V). This further allows the indicators 105 on the housing 102 to signal a need for a recharge of the system 100 at different times. For example, if a catheter is not connected to the port 104, the pressure will be zero (i.e., 1 ATM) and therefore the indicator will turn red, signaling to the user that the catheter is currently connected. In another example, if the catheter is connected to the port 104 and inserted into the patient, a positive pressure may register and cause the indicator to signal a recharge to place the desired amount of air into the system. Alternately the form of the pressure wave can be monitored to determine if the catheter is connected to the port 104.

Figure 2:
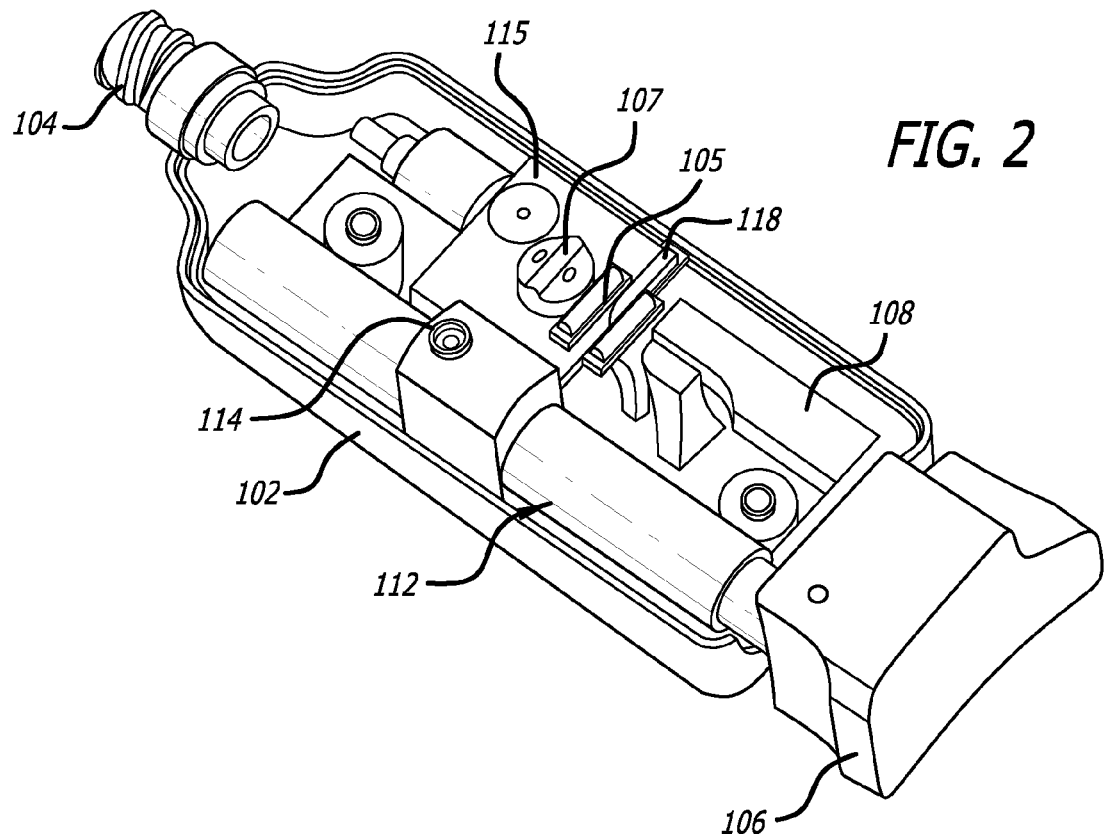
FIG. 2 illustrates a perspective view of the internal components of a body housing of the system of FIG. 1.
Figure 3:
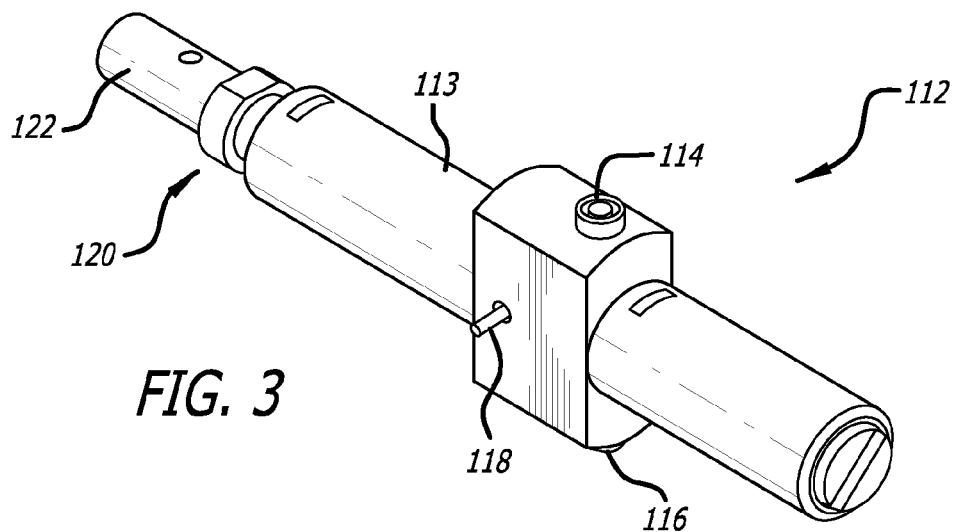
FIG. 3 illustrates a perspective view of piston members and piston cylinders from FIG. 2.

FIG. 2 illustrates an internal view of the housing 102 and some of its components. The monitor cable 108 enters the housing 102 and connects to electronics, such as a microprocessor, that are in communication with the transducer 115. Hence, the electronics can communicate with both the transducer 115 and the pressure monitor. The transducer 115 preferably includes a manifold 107 over its top which provides a connection interface for a tube (not shown) with the port 104. This passage through the port 104 and the transducer 115 within the housing 102 is further connected to a charging assembly 112 via connecting passage 118 (FIG. 3). Hence, as the handle 106 is moved out and in, the air passage of the system 100 is charged with a predetermined amount of air.

Figure 4:
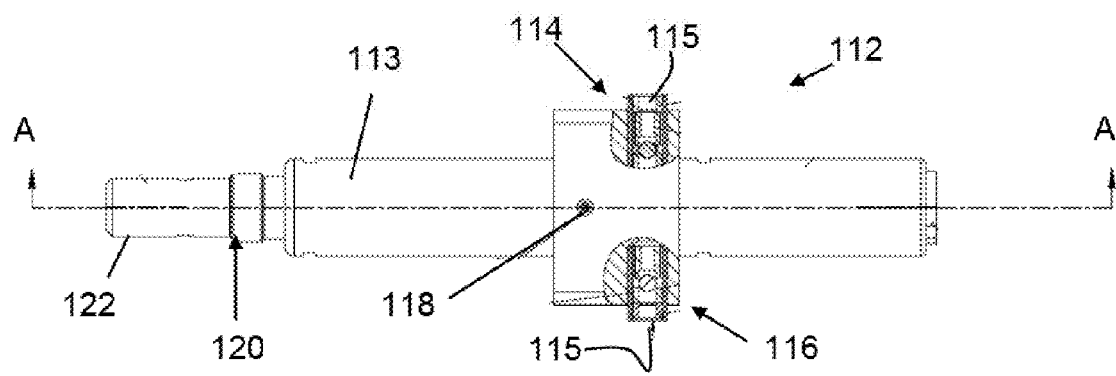
FIG. 4 illustrates a side view of the piston members and piston cylinders from FIG. 3.

FIGS. 3 and 4 illustrate various views of the charging assembly 112. Preferably, the charging assembly 112 is composed of an outer piston housing or piston cylinder 113 through which a piston member 120 moves into and partially out of. Preferably, this piston cylinder 113 is generally cylindrical in shape. The piston member 120 is connected to the handle 106 at end 122.

As described in more detail below, the charging assembly 112 achieves a desired air pressure through passage 118 by the movement of the piston member 120 and two check valves 114 and 116 that are set to open at different pressures. Preferably, these check valves also include air filters 115 to prevent any particles, dirt or other contamination into the system (FIG. 4).

Figure 5:
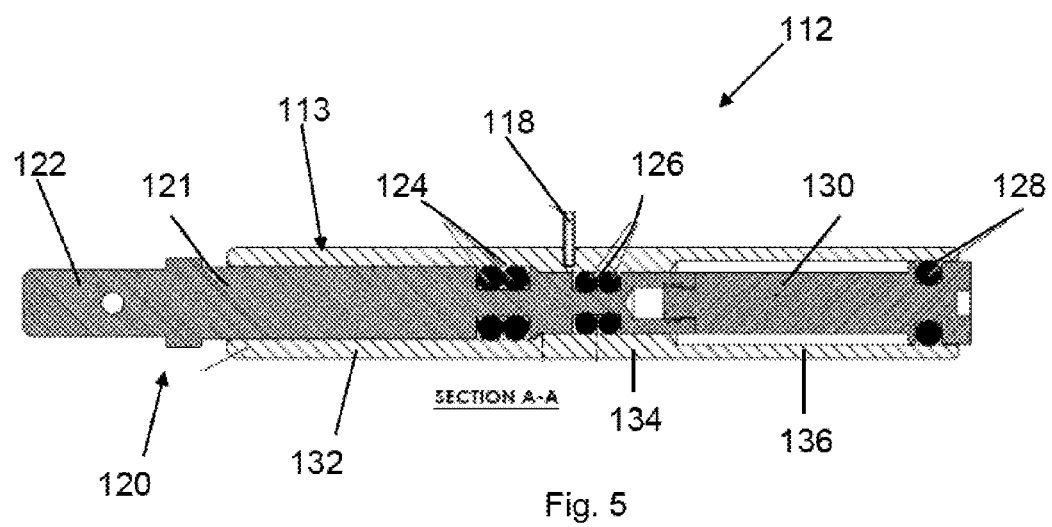
FIG. 5 illustrates a cross sectional view of the piston members and piston cylinders from FIG. 4 taken along lines A-A.

Turning to FIG. 5, a cross sectional view of the charging assembly 112 is shown. The piston member 120 preferably includes a first section 121 adjustably connected to a second section 130 (e.g., via a thread) to allow the length of the piston member 120 to be adjusted. As will become clear with the explanation below, this adjustment can modify an amount of air moved by the piston member 120. Also, this threading allows the piston member 120 to be easily assembled within the housing 113.

The piston member 120 also includes at least three sealing members (e.g., o-rings): a first sealing member 124, a second sealing member 126 and a third sealing member 128. These sealing members 124, 126 and 128 contact an inner surface of the housing 113 so as to prevent passage of air and create two sealed air spaces between each other. Preferably, these sealing members are located in recessed areas of the piston member 120 and are composed of fluroelastomer (Viton).

Preferably, the passage within the housing 113 has three different areas of different diameter: area 132, area 134 and area 136. Preferably area 134 is located between the other two areas 132 and 136 and has a smaller diameter than these two areas 132 and 136. Since the piston member 120 also has areas of different diameters, the piston member 120 is restricted from moving (i.e., restricted from being pushed in or pulled out beyond a predetermined position).

The section 134 also includes an opening in communication with passage 118, through which air is pulled from or pushed into the air passage of the system 100. Further, this area is coupled to the first check valve 114 configured to allow outside air to enter the system at a predetermined air pressure and the second check valve 116 configured to allow air in the housing 113 to be released into the outside environment at a predetermined air pressure. In other words, the first check valve 114 opens at a predetermined negative pressure and the second check valve 116 opens at a predetermined positive pressure. For example, the valve 114 may open when a pressure in the housing 113 reaches −0.5 PSI and the valve 116 may open when a pressure in the housing 113 reaches +0.5 PSI.

Figure 6:
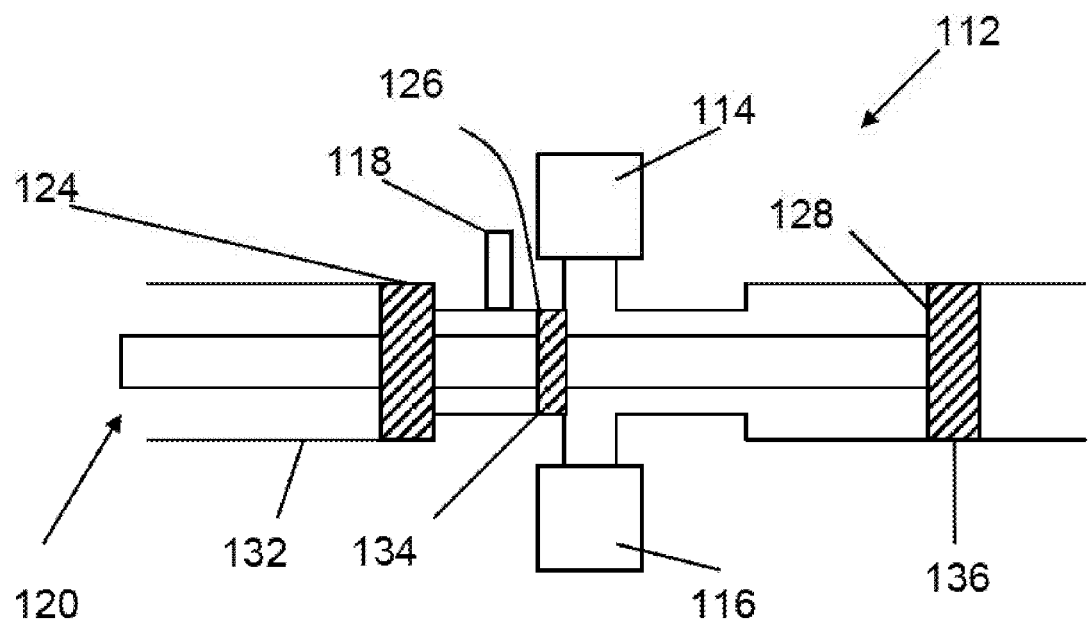
FIGS. 6-8 illustrate simplified cross sectional views of the piston members in various positions within the piston cylinders; and, FIG. 9 is an example pressure graph of an air management system according to a preferred embodiment of the present invention.
Figure 7:
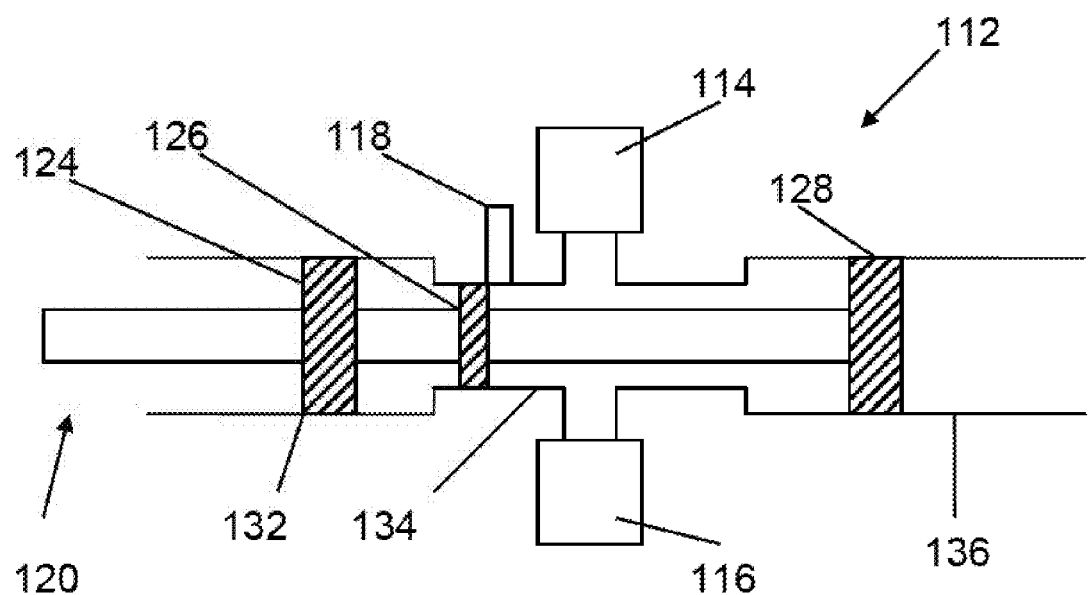
Figure 8:
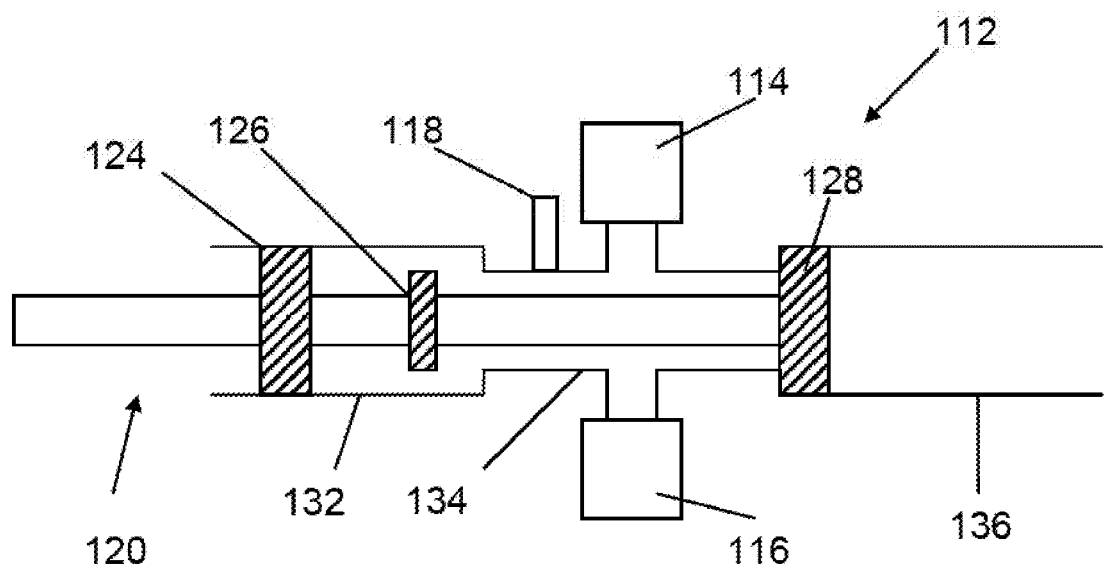

FIGS. 6-8 illustrate a simplified drawing of the charging assembly 112 in various positions. Beginning with FIG. 6, the piston member 120 is illustrated in a "pushed in" position (i.e., the handle 106 is located near the housing 102). In this position, the passage 118 is isolated by sealing members 124 and 126, preventing air from entering or leaving the passage of the system 100.

As seen in FIG. 7, as the user begins to pull out the piston member 120, air within the larger-volume area 136 is forced into the smaller volume area of area 134, thereby increasing the air pressure. Once the air pressure between the sealing members 126 and 128 reaches a predetermined positive pressure, the check valve 116 releases any excess air to maintain a pressure at the predetermined positive pressure. As the piston member 120 continues to be pulled out, the sealing member 126 passes the passage 118 and therefore opens the area between sealing members 126 and 128 to the air passage of the system 100 (i.e., the passage 118, the air passage of the catheter and the transducer 115). Since the air pressure has been limited by the check valve 116, the pressure lumen or bladder on the pressure measuring catheter is not damaged. Hence, the predetermined opening pressure of this check valve 116 (and as discussed below valve 114) should be selected, in part, based on the pressure rating of the pressure catheter.

In FIG. 8, the piston member 120 is pulled out from the charging assembly 112 as far as possible. In this position, the area between the sealing member 124 and sealing member 126 becomes open to the air passage of the system 100 (i.e., the passage 118, the air passage of the catheter and the transducer 115). In this respect, the area between sealing member 124 and 128 is at about the positive predetermined positive pressure that check valve 116 opens (e.g., +0.5 PSI).

Once the piston member 120 has been pulled out as far as it will go, it can be pushed back in. Returning once again to FIG. 7, as the piston member 120 is pushed in, the sealing member 126 once again engages area 134. The air between sealing member 126 and 128 moves from smaller diameter region 134 to larger diameter region 136 and therefore reduces the pressure in the system 100. As the pressure reaches a negative predetermined amount (e.g., −0.5 PSI), the check valve 116 opens to let in additional air to maintain that predetermined pressure. Hence, the passages of the system 100 remain at the predetermined air pressure.

As the piston member 120 continues to be pushed inwards, pressure builds between sealing member 124 and 126 as the air moves from the larger diameter region 132 to the smaller diameter region 134. As seen in FIG. 6, the sealing member 126 passes passage 118, allowing the high pressure air between sealing members 124 and 126 to pass into the system 100. In this respect, the system 100 progresses from a predetermined negative pressure followed by the injection of a known volume of air, since the volume of air between the sealing members 124 and 126 is added to the system 100. In other words, system 100 has been evacuated to a defined negative pressure, then injected with a predetermined quantity of air.

Figure 9:
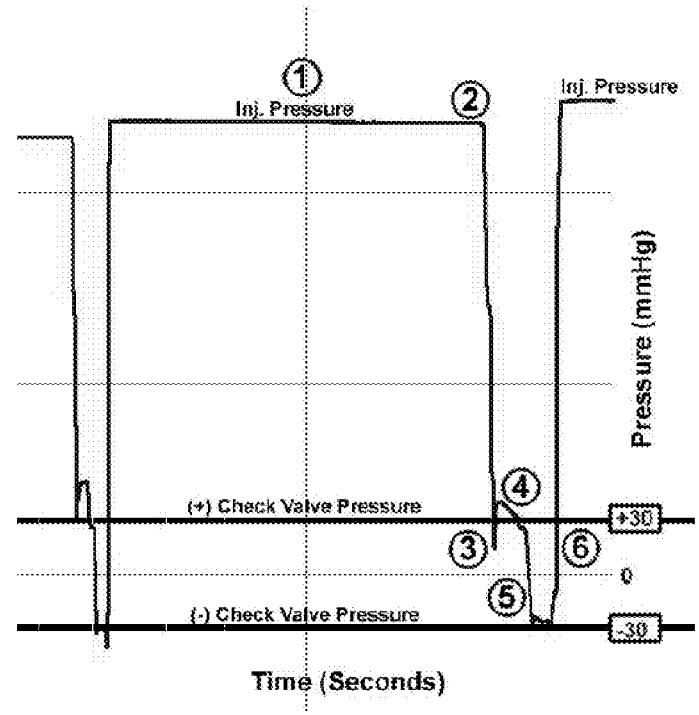

FIG. 9 illustrates an example pressure wave measurement of an air management system during movement of the piston member 120. For example, area 1 illustrates the pressure after full injection of the known air volume of the piston member 120. Area 2 illustrates the initial retraction of the piston member where pressure decreases due to volume increases in the housing 113 (the system remains isolated from the check valve). Area 3 illustrates a continued retraction as the system pressure increases due to volume decreases in the housing 113 (the check valve 116 maintains a position predetermined pressure). Area 4 illustrates the initial actuation inwards of the piston member 120 where the pressure is maintained. Area 5 illustrates the continued inward movement of the piston member 120 where the check valve 114 limits the negative pressure. Finally, area 6 illustrates the final movements of the piston member 120 as the known volume of air is injected back into the system (i.e., the catheter).

Depending on the predetermined opening pressure of the check valves 114 and 116, the diameter of the areas 132, 134 and 136, and the spacing of the sealing members 124, 126 and 128, the final pressure in the system can be determined. The injection volume is equal to the area between sealing member 124 and 126 times the distance from transition of area 132 to area 134 and the final location of 126 at the end of the stroke. Preferably, this final pressure is a value that allows the transducer and the bladder/lumen on the distal end of the measurement catheter to achieve accurate results. In this respect, a second shut off valve, which is typically required in use with prior art air management systems, is unnecessary.

In one example, the sealing members 124 and 126 are spaced at about 0.4064 cm (0.160 inchesI from each other and sealing members 126 and 128 are spaced at about 2.032 cm (0.800 inches) from each other. The diameter of the piston member 120 between the sealing members 124 and 126 is about 0.51816 cm (0.204inche) and the diameter of the piston member 120 between the sealing members 126 and 128 is about 0.43942 cm (0.173 inches). The diameter of the first area 132 is about 0.5207 cm (0.205 inches), the diameter of the second area 134 is about 0.43942 cm (0.173 inches) and the diameter of the third area 136 is about 0.60452cm (0.238inched).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A catheter air management system comprising:
   a piston cylinder having a piston passage;
   a first check valve connected to said piston passage and further configured to open at a predetermined positive pressure;
   a second check valve connected to said piston passage and further configured to open at a predetermined negative pressure;
   a catheter passage connected to said piston passage and a pressure transducer and connectable to a pressure measurement catheter; and,
   a piston member disposed within said piston passage;
   wherein movement of said piston member within said piston passage evacuates air to a predetermined negative pressure from said catheter passage and further injects a predetermined volume of air within said catheter passage.

2. The catheter air management system of claim 1, wherein said piston member further comprises three sealing members disposed along a length of said piston member.

3. The catheter air management system of claim 2, wherein said piston passage has a first area having a first diameter, a second area having a second diameter, and a third area having a third diameter.

4. The catheter air management system of claim 3, wherein said second area is disposed between said first area and said third area and wherein said second area has a diameter smaller than that of said first area and said third area.

5. The catheter air management system of claim 4, wherein said catheter passage and said first check valve and said second check valve have openings located in said second area.

6. The catheter air management system of claim 5, further comprising a body housing containing said piston cylinder.

7. The catheter air management system of claim 6, wherein said body housing further comprises an indicator that signals when to activate said catheter air management system to recharge an air volume.

8. An air management system for a catheter comprising:
   a piston cylinder having a piston passage disposed therein;

a pressure relief mechanism for relieving pressure above or below predetermined pressures within a portion of said piston passage;

a pressure communication passage connected to a pressure transducer and connectable to a pressure sensing catheter; and, a piston member slidably positioned in said piston passage;

wherein movement of said piston member within said piston passage adjusts a pressure level of air inside said pressure communication passage and further injects a predetermined volume of air inside said pressure communication passage.

9. The air management system of claim 8, wherein said predetermined pressures of said pressure relief mechanism are selected from pressures above and below ambient atmosphere pressure.

10. The air management system of claim 9, wherein said pressure relief mechanism further comprises a first check valve mechanism configured to open at a positive pressure relative to said ambient atmosphere pressure and a second check valve mechanism configured to open at a negative pressure relative to said ambient atmosphere pressure.

11. The air management system of claim 8, wherein said piston member further comprises a first sealing member, a second sealing member and a third sealing member.

12. The air management system of claim 11, wherein said piston member is positionable to create a single compartment between said first sealing member and said second sealing member and wherein said piston member is positionable to create two compartments between said first and second sealing member and between said second and third sealing member.

13. The air management system of claim 12, wherein said second sealing member has a diameter that is smaller than a diameter of said first sealing member or said third sealing member.

14. The air management system of claim 13, further comprising a body housing enclosing said piston cylinder.

15. The air management system of claim 14, further comprising an indicator disposed on said body housing so as to signal when said pressure level of air inside said pressure communication passage should be adjusted.

16. An air management system for a catheter comprising:
a piston cylinder having a piston passage disposed therein;
a pressure transducer;
a pressure communication passage connected to said pressure transducer and selectively connectable to a pressure catheter and a pressure monitor; and,
a piston member movably disposed in said piston passage;
wherein movement of said piston member within said piston passage first adjusts a pressure within said pressure communication passage to a predetermined negative air pressure and second adjusts said pressure within said pressure communication passage to a predetermined positive air pressure.

17. The air management system of claim 16, further comprising a first check valve and a second check valve in communication with said piston passage.

18. The air management system of claim 17, further comprising a plurality of sealing members disposed along the length of said piston member.

19. The air management system of claim 18, wherein said piston passage has multiple areas that each have different diameters.

20. The air management system of claim 19, wherein at least one of said plurality of sealing members has a diameter different from the remaining sealing members of said plurality of sealing members.

* * * * *